United States Patent [19]

Ratton

[11] Patent Number: 4,727,182

[45] Date of Patent: Feb. 23, 1988

[54] PREPARATION OF MONOHALOHYDROQUINONE MONOCARBOXYLATES/DICARBOXYLATES

[75] Inventor: Serge Ratton, Villefontaine, France

[73] Assignee: Rhone-Poulenc Specialites Chimiques, Courbevoie, France

[21] Appl. No.: 748,424

[22] Filed: Jun. 25, 1985

[30] Foreign Application Priority Data

Jun. 25, 1984 [FR] France .......................... 84 10183

[51] Int. Cl.$^4$ .................. C07C 69/017; C07C 69/28; C07C 69/16; C11C 3/00
[52] U.S. Cl. .................................. 560/144; 260/408
[58] Field of Search .................. 560/144; 260/410.5, 260/408

[56] References Cited

U.S. PATENT DOCUMENTS 2,588,978  3/1952  Gearhart et al. .................. 560/109

OTHER PUBLICATIONS

Diana et al., J. Med. Chem., vol. 20, No. 6, pp. 757-761, 1977, RS 1J5.
Levy et al., Annalen, vol. 210, p. 140 (1881).
Schied et al., Annalen, vol. 218, p. 213 (1883).
van Erp, Ber., vol. 58, p. 664 (1925).

Primary Examiner—Donald B. Moyer
Assistant Examiner—Patricia M. Scott
Attorney, Agent, or Firm—Burns, Doane, Swecker & Mathis

[57] ABSTRACT

Monohalohydroquinone monocarboxylates are selectively prepared by halogenating a hydroquinone monocarboxylate, or admixture thereof with a hydroquinine dicarboxylate and a minor amount of hydroquinone, with a chlorine, bromine or sulfuryl halide halogenating agent; such monocarboxylates are facilely converted into the corresponding dicarboxylates by acylation. Both the monocarboxylates, e.g., monochlorohydroquinone monoacetate, and dicarboxylates, e.g., monochlorohydroquinone diacetate, are useful organic intermediates.

34 Claims, No Drawings

PREPARATION OF MONOHALOHYDROQUINONE MONOCARBOXYLATES/DICARBOXYLATES

BACKGROUND OF THE INVENTION

1. Field of the Invention

The present invention relates to the preparation of monohalohydroquinone monocarboxylates from hydroquinone monocarboxylates (more particularly of monochlorohydroquinone monocarboxylates from hydroquinone monocarboxylates), and to the use of such monocarboxylates for the preparation of monohalohydroquinone dicarboxylates and in particular monochlorohydroquinone dicarboxylates.

2. Description of the Prior Art

Monohalohydroquinone dicarboxylates and in particular monochlorohydroquinone dicarboxylates are important industrial compounds especially useful for the preparation of aromatic polyesters (cf. U.S. Pat. No. 4,118,372 and French Patent Application No. 79-24,135, published under No. 2,465,758) or as intermediates for the preparation of monohalohydroquinones, and especially of monochlorohydroquinone, which are employed as photographic developers (cf. U.S. Pat. Nos. 2,748,173 and 1,912,744).

Various methods for the production of monochlorohydroquinone dicarboxylates exist, which differ from each other in the nature of the starting materials. Thus, it has been proposed to prepare monochlorohydroquinone diacetate from benzoquinone. According to a first method, a reductive acetylation of chlorobenzoquinone is carried out [cf. J. Cason et al, *J. Org. Chem.*, 15, 860–4 (1950)]. In a second method, simultaneous chlorination and reductive acetylation of benzoquinone are carried out by reacting the latter either with acetyl chloride, optionally in the presence of zinc [cf. Schied, *Annalen*, 218, page 213 (1883); G. A. Varvoglis, Ber., 70, page 2396 (1937); H. Burton et al, *J. Chem. Soc.*, pages 2546–48 (1952)], or with acetic anhydride in the presence of zinc chloride [cf. Thiele et al, *Annalen*, 311, page 344 (1900); H. Burton et al, *J. Chem. Soc.*, pages 755–59 (1952)]. These various methods are of no industrial interest, on the one hand because of their poor selectivity (they result in concurrent formation of large amounts of dichloro derivatives and of hydroquinone diacetate) and, on the other hand, because of the very fact that benzoquinone is used as a starting material. This is why the process of greatest industrial interest consists of preparing monochlorohydroquinone diacetate from hydroquinone, a common industrial product. This process comprises a stage of chlorination of hydroquinone to monochlorohydroquinone, followed by a stage of acetylation of the monochlorohydroquinone. This latter stage does not present any particular problem because the yields of monochlorohydroquinone diacetate are quantitative; the acetylating agent employed is acetyl chloride [Schied, loc. cit.]or acetic anhydride [cf. Levy et al, *Annalen*, 210, page 140 (1881); Van Herp, Ber., 58, page 664 (1925)]. On the other hand, the implementation of the chlorination stage is found to require more care, and the manner of carrying it out determines the quality of the final product. In fact, the various methods of chlorination of hydroquinone which have been used entail the concurrent formation of large amounts of dichlorohydroquinones which are difficult to separate from monochlorohydroquinone and which result in the formation of dichlorohydroquinone diacetates after acetylation, which are themselves also difficult to separate from monochlorohydroquinone diacetate. The problem of selective chlorination of hydroquinone to monochlorohydroquinone is an old one (cf. U.S. Pat. No. 1,912,744) and it to date has not been possible to solve it in a wholly satisfactory manner. In U.S. Pat. No. 2,748,173 it was proposed to carry out the chlorination of hydroquinone by reacting gaseous chlorine with a solution of hydroquinone in aqueous acetic acid; despite the precautions taken (use of a deficiency of chlorine which results in an incomplete degree of conversion of hydroquinone) the formation of dichlorohydroquinones remains high. In Japanese patent application published under No. 56/45,433 it was proposed to solve this problem by carrying out the chlorination with the aid of a 5N aqueous solution of hydrochloric acid in the presence of ferric or cupric chlorides and of a gas containing oxygen under pressure. Although this process makes it possible to restrict the formation of dichlorohydroquinones, its industrial interest is diminished by the need to operate under oxygen pressure and to require the presence of metal salts which promote the oxidation of hydroquinone to quinone.

As a result, serious industrial need still exists for a process for the preparation of monohalohydroquinone dicarboxylates in a selective manner, and more particularly for the preparation of monochlorohydroquinone dicarboxylates. Cf. U.S. Pat. No. 2,588,978.

SUMMARY OF THE INVENTION

Accordingly, a major object of the present invention is the provision of a selective process for the preparation of monohydroquinone monocarboxylates which are themselves useful for the production of monohalohydroquinone dicarboxylates, and especially monochlorohydroquinone dicarboxylates, or for the production of monohalohydroquinones, if appropriate.

Thus, one object of the present invention is the provision of a selective process for the preparation of monohalohydroquinone monocarboxylates.

Another object of this invention is the use of the monohalohydroquinone monocarboxylates thus prepared as intermediates in the production of monohalohydroquinone dicarboxylates.

More specifically, this invention firstly features a process for the preparation of monohalohydroquinone monocarboxylates which is characterized in that the halogenation of a hydroquinone monocarboxylate, optionally mixed with a hydroquinone dicarboxylate and a minor amount of hydroquinone, is carried out using a halogenating agent selected from among chlorine, bromine or sulfuryl halides in a substantially anhydrous carboxylic acid.

DETAILED DESCRIPTION OF THE INVENTION

More particularly according to the present invention, it has now unexpectedly and surprisingly been determined the monocarboxylates can be very selectively halogenated under the aforesaid conditions, in contrast to hydroquinone. The monohalohydroquinone monocarboxylates thus obtained can be readily converted in the halogenation reaction medium to monohalohydroquinone dicarboxylates, by acylation. The linking of these two steps or stages thus constitutes a convenient and selective means for preparing monohalohydroquinone dicarboxylates.

The process of the invention is especially suitable for the preparation of monohalohydroquinone monocarboxylates and monohalohydroquinone dicarboxylates having the general formulae:

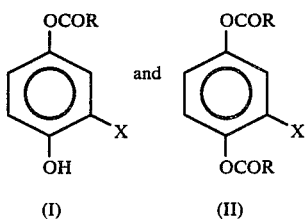

in which R is a straight or branched chain alkyl radical containing from 1 to 4 carbon atoms, and X is a chlorine or bromine atom, from hydroquinone monocarboxylates having the general formula:

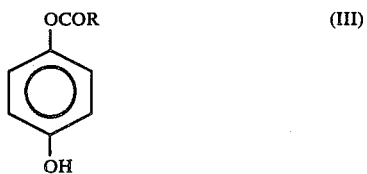

in which R is as defined above.

Methyl, ethyl, n-propyl, isopropyl, n-butyl and isobutyl radicals are representative examples of the radicals R.

As specific examples of the hydroquinone monocarboxylate starting materials, representative are hydroquinone monoacetate, propionate, n-butyrate and isobutyrate.

In general, halogenation of the hydroquinone monocarboxylates can be carried out under conditions which are typically employed to substitute a halogen atom for a hydrogen atom in an aromatic nucleus by means of chlorine, bromine or sulfuryl halide.

The amount of halogenating agent is typically close to the stoichiometry of the reaction, namely, approximately that amount required in theory to introduce one halogen atom per mole of hydroquinone monocarboxylate. It would not constitute a departure from the scope of the present invention to use a slight stoichiometric deficiency or excess of halogenating agent. From a practical standpoint, an amount of halogenating agent which is in the range of 0.5 to 1.5 mole per mole of hydroquinone monocarboxylate is quite suitable.

The temperature at which the halogenation reaction is carried out can vary over wide limits; in general, it is in the range of 0° to 120° C. and preferably from 10° to 100° C.

As the substantially anhydrous carboxylic acid reaction medium, acids which are good solvents for hydroquinone monocarboxylates, hydroquinone dicarboxylates and hydroquinone are preferably used, and which additionally are stable and liquid under the reaction conditions. "Substantially anhydrous acids" connotes acids containing less than 5% by weight of water and preferably less than 2% by weight. More particularly, straight or branched chain alkanoic acids containing from 1 to 8 carbon atoms are advantageously used, such as formic, acetic, propionic, butyric, isobutyric, 2-methylbutanoic, 2-ethylbutanoic, 2,2-dimethylbutanoic, pentanoic, 2-methylpentanoic, 5-methylpentanoic, hexanoic, or 2-ethylhexanoic acids. For the sake of convenience, the lower alkanoic acids containing from 1 to 4 carbon atoms are preferably used. The carboxylic acid from which the hydroquinone monocarboxylate is derived is most preferably employed.

The concentration of the hydroquinone monocarboxylate in the carboxylic acid is not critical and can vary over wide limits. Its choice depends essentially on practical considerations geared to reaching a compromise between a maximum possible output from the apparatus and good stirrability of the reaction mixture.

The hydroquinone monocarboxylates may be employed either alone or mixed with hydroquinone dicarboxylates and minor amounts of hydroquinone, if appropriate. Since it is not easy to obtain hydroquinone monocarboxylates devoid of the dicarboxylates [to do this, it is necessary to employ complicated preparative methods, such as that described by H. S. Olcott, *J. Am. Chem. Soc.*, 59, pages 392–393 (1937)], it is preferable to apply the process of the invention to mixtures of hydroquinone monocarboxylates, hydroquinone dicarboxylates and, if appropriate, which are obtained by partial acylation of hydroquinone with acylating agents such as acid anhydrides and halides [cf. F. D. Chattaway, *J. Chem. Soc.*, pages 2495–96 (1931); d. Johnston, *Chem. and Ind.*, page 1000 (1982)] or by a disproportionation reaction between hydroquinone and hydroquinone dicarboxylates. The use of such mixtures is found to be especially advantageous because it has been observed that hydroquinone dicarboxylates remain practically unhalogenated during the halogenation and consequently do not give rise to dihalo derivatives. Similarly, the presence of a small amount of hydroquinone does not prejudice the selectivity of halogenation. Upon completion of the reaction the monohalohydroquinone monocarboxylate is separated from the other components of the mixture. When the reaction mixture from the halogenation reaction is subjected to acylation, the monohalohydroquinone which may have formed during the halogenation (and which may be accompanied by very small amounts of dihalohydroquinones) is converted to a monohalohydroquinone dicarboxylate; the monohalohydroquinone dicarboxylate is then separated from all of the hydroquinone dicarboxylate, which latter may be reused for the preparation of the mixture of hydroquinone monocarboxylate and hydroquinone dicarboxylate.

The use of mixtures of hydroquinone monocarboxylate and hydroquinone dicarboxylate containing minor amounts of hydroquinone to carry out the process of the invention is thus found to be especially advantageous and consequently circumscribes another object of the present invention. The use of mixtures of hydroquinone monocarboxylates, hydroquinone dicarboxylates and hydroquinone originating from the disproportionation reaction of a hydroquinone dicarboxylate with hydroquinone is a preferred embodiment of the process for the preparation of monohalohydroquinone monocarboxylates according to this invention. This reaction may be represented by the following reaction mechanism:

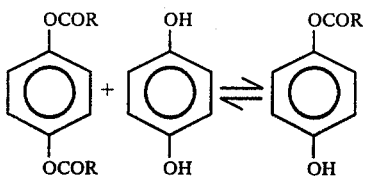

(1)

in which R is as defined above.

To satisfactorily carry out the aforesaid reaction, amounts of hydroquinone dicarboxylates and hydroquinone are used which are calculated to shift the equilibrium denoted by the scheme (1) as far as possible to the right. In order to restrict as much as possible the amount of hydroquinone present in the mixture subjected to halogenation and, consequently, the formation of dihalohydroquinones, the process is carried out in the presence of a stoichiometric excess of hydroquinone dicarboxylate, since the latter is practically unreactive during the halogenation. The excess hydroquinone dicarboxylate required to obtain a final product containing as few dihalo derivatives as possible depends upon the purity of the final product which is required and upon the conditions of the disporportionation and halogenation reactions. In general, it is preferable to employ an excess of at least 0.5 mole of hydroquinone dicarboxylate vis-a-vis the stoichiometry of the disproportionation reaction; there is no critical upper limit on the excess of hydroquinone dicarboxylate; however, the use of too great an amount of hydroquinone dicarboxylate would result in a lowering of the productivity of the reaction and in high costs of separation of the hydroquinone dicarboxylates. For these reasons, there is no need for the excess of hydroquinone dicarboxylate to be greater than 4 moles relative to the stoichiometric amount. In sum, the amount of hydroquinone dicarboxylate employed in the disproportionation stage is at least 1.5 mole per mole of hydroquinone; it is preferably in the range of from 1.5 to 5 moles per mole of hydroquinone.

The disproportionation reaction may be carried out in bulk or in any organic medium which is inert under the reaction conditions. Solvents for the reactants are preferably used. Especially suitable are carboxylic acids which are liquid under the conditions of the reaction, aliphatic or arylaliphatic ethers such as isopropyl ether, dibutyl ether, and anisole; heterocyclic ethers such as tetrahydrofuran and dioxane; saturated aliphatic (n-hexane), alicyclic (cyclohexane), aromatic (benzene, toluene), hydrocarbons, or their halogenated derivatives; carbon tetrachloride, methylene chloride, chloroform, or chlorobenzene. The same carboxylic acids as those abovementioned for the halogenation stage may be employed. More particularly, the lower alkanoic acids and particularly acetic acid, these being preferably anhydrous, are advantageously used. The concentration of reactants in the reaction medium is not critical.

The temperature of the disproportionation reaction can also vary over wide limits. Temperatures in the range of from 50° to 250° C. and preferably from 80° to 180° C. are generally quite suitable. The reaction may be carried out at normal pressure or under pressure; when the temperature selected is higher than the boiling point of some of the components of the mixture the process may be carried out under the autogenous pressure of the reactants.

When the disproportionation is carried out in a carboxylic acid the process may take place in the presence or absence of a catalyst. When a catalyst is employed, strong inorganic or organic acids are preferably used, namely, acids which have a pK of below 1 in water at 25° C. Preferably used are sulfuric acid and sulfonic acids, such as methanesulfonic, di- and trifluoromethanesulfonic, benzenesulfonic, toluenesulfonic, naphthalenesulfonic acids, or sulfonic resins.

The amount of strong acid, expressed in equivalents of protons per mole of hydroquinone can vary over wide limits. In general, it ranges from 0.0001 to 0.2 equivalent of proton per mole of hydroquinone.

When a solvent other than an acid, and particularly an ether, is employed, the process may be carried out in the presence of a catalyst of the type of those which are employed in transesterification reactions. For this purpose the organic nitrogenous bases may be used, such as primary, secondary or tertiary amines and heterocyclic bases; representative are diethylamine, ethylamine, triethylamine, n-propylamine, diisopropylamine, triethanolamine, pyridine and piperidine. Alkali metal carboxylates may also be used, such as K, Li or Na acetates and Lewis acids, such as those mentioned in G. A. Olah, *Friedel-Crafts Reaction*, volume 1, pages 191 to 291. Zinc, titanium, manganese or cobalt salts or of metal alkoxides are preferably used. Representative are zinc halides such as $ZnCl_2$; alkyl titanates such as methyl, ethyl, n-propyl, isopropyl, n-butyl and isobutyl titanates; Mn and Co carboxylates such as Mn and Co acetate, propionate and isobutyrate.

The amount of catalyst, expressed in moles of base or Lewis acid per mole of hydroquinone, may be in a range from 0.0001 to 0.2 mole per mole of hydroquinone.

The disproportionation reaction is preferably carried out in a carboxylic acid and, still more preferably, in the same carboxylic acid as that employed in the stage of halogenation of the mixture, since the strong acid which may be employed as a catalyst does not in any way hinder the progress of the halogenation. Preferably used is the acid corresponding to that from which the carboxylates are derived. It is then particularly advantageous to conjoin the disporportionation stage with the halogenation stage. Compare generally my copending application, Ser. No. 748,454 filed concurrently herewith on June 25, 1985, and assigned to the assignee hereof.

Another object of the present invention consequently features a process for the preparation of monohalohydroquinone monocarboxylates according to which, in a first stage, a mixture of hydroquinone monocarboxylates, hydroquinone dicarboxylates and a minor amount of hydroquinone is prepared by reacting hydroquinone with a stoichiometric excess of hydroquinone dicarboxylates in a substantially anhydrous carboxylic acid, optionally in the presence of a strong acid and then, in a second stage, the reaction mixture from the disproportionation reaction is subjected to halogenation by means of chlorine, bromine or a sulfuryl halide.

From a practical standpoint, the halogenation is carried out simply by gradual addition of the halogenating agent to the carboxylic acid solution of hydroquinone monocarboxylate and optionally of hydroquinone dicarboxylate and hydroquinone, which is maintained at a suitable temperature. Upon completion of the reaction the various components of the reaction mixture may be separated, for example by distillation, or, alternatively, according to another preferred embodiment of the invention, treated with an acylating agent to convert the monohydroquinone monocarboxylate.

More specifically, yet another object of the present invention is a process for the preparation of monohalohydroquinone dicarboxylates, according to which, in a first step, halogenation of a hydroquinone monocarboxylate or a mixture of hydroquinone monocarboxylates, hydroquinone dicarboxylate and a minor quantity of hydroquinone, to monohalohydroquinone monocarboxylate, is carried out by means of a halogenating agent selected from among chlorine, bromine or sulfuryl halide, and then, in a second stage, acylation of the hydroquinone monocarboxylate is carried out by means of an acylating agent, optionally in the presence of a strong acid.

The similarity of the reaction media therefore makes it possible to interlink the halogenation and acylation stages without separation of the halogenation reaction products.

In the same manner it is possible to conjoin the stages of preparation of mixtures of hydroquinone monocarboxylates, hydroquinone dicarboxylates and hydroquinone, in particular by disproportionation, and the halogenation and acylation stages.

Another object of the present invention is therefore a process for the preparation of monohalohydroquinone dicarboxylates according to which, in a first stage, a mixture of hydroquinone monocarboxylate, hydroquinone dicarboxylate and a minor amount of hydroquinone is prepared by reacting hydroquinone with a stoichiometric excess of hydroquinone dicarboxylates in a substantially anhydrous carboxylic acid, optionally in the presence of a strong acid and then, in a second stage, the reaction mixture from the disproportionation reaction is subjected to halogenation by means of chlorine, bromine or a sulfuryl halide and, finally, in a third stage, acylation of the monohalohydroquinone monocarboxylates present in the halogenation reaction medium is carried out by means of an acylating agent and optionally in the presence of a strong acid.

Acid anhydrides and halides and preferably chlorides are used as acylating agent for the monohalohydroquinone monocarboxylates. The anhydrides are preferred. Although it is possible to prepare mixed monohalohydroquinone dicarboxylates, without departing from the scope of the present invention, by using an anhydride or a halide of an acid other than that employed to obtain the starting hydroquinone monocarboxylate, it is preferred to use an anhydride or a halide derived from the same acid. Acetic, propionic and butyric anhydrides and acetyl, propionyl and butyryl chlorides are representative acylating agents.

The amount of acylating agent is preferably close to the stoichiometric amount required to acylate the phenolic hydroxyls present, namely, approximately 1 mole of acylating agent per hydroxyl group to be acylated. However, it is possible to use a slight stoichiometric deficiency or excess of acylating agent without departing from the scope of the present invention. The amount of acylating agent may preferably be in the range of from 1 to 5 moles per hydroxyl group to be acylated. When the mixture subjected to halogenation contains hydroquinone, the amount of acylating agent is preferably sufficient to completely acylate the residual hydroquinone and/or the halohydroquinones present in the halogenation medium to hydroquinone dicarboxylates.

The temperature of the acylation reaction depends upon the nature of the acylating agent. In general it ranges from 0° C. to 200° C., and preferably from 20° C. to 120° C.

When an acid anhydride is used as an acylating agent, the process may be carried out in the presence or in the absence of any catalyst. When a catalyst is employed, a strong acid is preferably used. For this purpose, acids having a pK of below 1 in water at 25° C. are used. Preferably used are inorganic acids, such as sulfuric acid, or of sulfonic acids, such as methanesulfonic, difluoro- or trifluoromethanesulfonic, benzenesulfonic, toluenesulfonic or naphthalenesulfonic acids. When a mixture of mono- and dicarboxylates produced by a disproportionation reaction is used, the acid catalyst may originate from this stage. The amount of strong acid, expressed in equivalents of protons per hydroxyl group to be acylated may range from $1 \times 10^{-4}$ to $2 \times 10^{-1}$ and preferably from $1 \times 10^{-3}$ to $2 \times 10^{-2}$.

The reaction mixture which results from the acylation is treated according to the usual methods for separating the various components of the mixture. When, according to a preferred embodiment of the invention, the starting material used for the halogenation stage is a mixture of hydroquinone monocarboxylate, hydroquinone dicarboxylate and optionally hydroquinone, the reaction mixture resulting from the acylation essentially consists of the monohalohydroquinone dicarboxylate resulting from the acylation of the monohalohydroquinone monocarboxylate and optionally of the monohalohydroquinone and, where applicable, a minor amount of dihalohydroquinone dicarboxylate and the hydroquinone dicarboxylate initially present, which may also contain that originating from a possible acylation of residual hydroquinone. According to another preferred embodiment of the invention, the hydroquinone dicarboxylates are reused or recycled to prepare the initial mixture of hydroquinone monocarboxylate, hydroquinone dicarboxylate and optionally hydroquinone, which is employed in the halogenation stage, by a disproportionation reaction between a hydroquinone dicarboxylate and hydroquinone.

According to a first alternative method, the reaction mixture from the acylation is distilled to firstly separate the solvent acid, and optionally the excess acylating agent, the hydroquinone dicarboxylate and the monohalohydroquinone dicarboxylate. The hydroquinone dicarboxylate is recycled to the disproportionation reaction zone together with the carboxylic acid solvent. It suffices to add the amounts of hydroquinone and hydroquinone dicarboxylate which correspond to those consumed during the halogenation and, if appropriate, a suitable amount of a strong acid, to proceed to the preparation of the hydroquinone monocarboxylate.

According to a second alternative method, a sufficient amount of hydroquinone is added to the reaction mixture from the acylation to convert the excess acylating agent to hydroquinone dicarboxylate and then to proceed with the distillation of the reaction mixture and to recycle all the hydroquinone dicarboxylate and, if appropriate, the residual hydroquinone to the disproportionation stage.

The various alternative forms of the process according to the invention are especially highly suitable for selective preparation of monochlorohydroquinone diacetate which is essentially devoid of dichlorohydroquinone diacetate.

In order to further illustrate the present invention and the advantages thereof, the following specific examples are given, it being understood that same are intended only as illustrative and in nowise limitative.

EXAMPLE 1

14.6 g of the following mixture were charged into a 100 ml glass reactor equipped with a stirrer, thermometer, dropping funnel, vertical condenser and cooling bath:

| | | |
|---|---|---|
| (i) Hydroquinone monoacetate | 6 g | (0.0395 mole) |
| (ii) Hydroquinone diacetate | 8.34 g | (0.0430 mole) |
| (iii) Hydroquinone | 0.23 g | (0.002 mole) |
| (iv) Anhydrous acetic acid | 60 ml | |

5.61 g (0.0416 mole) of sulfuryl chloride were added dropwise thereto over 30 minutes while the temperature was maintained at 20° C.

The following results were obtained after assaying the reaction mixture by high-pressure liquid chromatography (HPLC):

| | | |
|---|---|---|
| (1) Hydroquinone monoacetate | 0.00605 | mole |
| (2) Monochlorohydroquinone monoacetate | 0.03475 | mole |
| (3) Hydroquinone diacetate | 0.0421 | mole |

The conversion of hydroquinone monoacetate was 84.7%.

The yield of monochlorhydroquinone monoacetate based on the hydroquinone monoacetate converted was 100%.

EXAMPLE 2

55.5 g of the following mixture was charged into a 500 ml reactor equipped as in Example 1:

| | | |
|---|---|---|
| (i) Hydroquinone monoacetate | 23.56 g | (0.155 mole) |
| (ii) Hydroquinone diacetate | 31.04 g | (0.160 mole) |
| (iii) Hydroquinone | 0.87 g | (0.0079 mole) |
| (iv) Acetic acid | 220 ml | |

Gaseous chlorine was introduced into the above mixture maintained at 20° C., at a rate of 5 l/hr for 54 minutes, i.e., 4.456 l (0.199 mole).

After analysis of the reaction mixture by HPLC, a mixture was obtained which contained:

| | | |
|---|---|---|
| (1) Hydroquinone monoacetate | 5.82 g | (0.0383 mole) |
| (2) Monochlorohydroquinone monoacetate | 21.82 g | (0.117 mole) |
| (3) 2,6-Dichlorohydroquinone monoacetate | 0.287 g | (0.0013 mole) |
| (4) Hydroquinone diacetate | 27.45 g | (0.1415 mole) |
| (5) Monochlorohydroquinone diacetate | 1.76 g | (0.0077 mole) |
| (6) 2,5-Dichlorohydroquinone diacetate | 0.58 g | (0.0022 mole) |
| (7) 2,3-Dichlorohydroquinone diacetate | 0.58 g | (0.0022 mole) |
| (8) Chlorohydroquinone | 0.88 g | (0.0061 mole) |

The yield of monochloro compounds (hydroquinone, monoester, diester) based on the reactants (hydroquinone, monoester and diester) converted was 92%.

EXAMPLE 3

The procedure was as in Example 2, but gaseous chlorine was introduced into the reaction mixture which was maintained at 80° C. The following products were found in the reaction mixture maintained at 80° C.

| | | |
|---|---|---|
| (1) Hydroquinone monoacetate | 6.795 g | (0.0447 mole) |
| (2) Monochlorohydroquinone monoacetate | 20.68 g | (0.1109 mole) |
| (3) 2,6-Dichlorohydroquinone monoacetate | 0.243 g | (0.0011 mole) |
| (4) Hydroquinone diacetate | 28.67 g | (0.1478 mole) |
| (5) Monochlorohydroquinone diacetate | 0.594 g | (0.0026 mole) |
| (6) 2,5-Dichlorohydroquinone diacetate | 1.762 g | (0.0067 mole) |
| (7) 2,3-Dichlorohydroquinone diacetate | 0.29 g | (0.0011 mole) |
| (8) Monochlorohydroquinone | 0.29 g | (0.0020 mole) |

The yield of monochloro compounds (hydroquinone, monoester, diester) based on the unchlorinated reactants (hydroquinone, monoester and diester) converted was 89%.

EXAMPLE 4

The procedure was as in Example 2, but gaseous chlorine was introduced for 56 minutes, 30 seconds, at a rate of 5 l/hr, i.e., 4.68 l (0.209 mole) into the reaction mixture, which was maintained at 20° C.

The following products were determined and identified in the reaction mixture using HBLC:

| | | |
|---|---|---|
| (1) Hydroquinone monoacetate | 3.28 g | (0.0216 mole) |
| (2) Monochlorohydroquinone monoacetate | 25.36 g | (0.136 mole) |
| (3) 2,6-Dichlorohydroquinone monoacetate | 0.3 g | (0.00135 mole) |
| (4) Hydroquinone diacetate | 28.32 g | (0.146 mole) |
| (5) Monochlorohydroquinone diacetate | 1.48 g | (0.0065 mole) |
| (6) 2,5-Dichlorohydroquinone diacetate | 0.89 g | (0.0034 mole) |
| (7) 2,3-Dichlorohydroquinone diacetate | 1.37 g | (0.0052 mole) |
| (8) Monochlorohydroquinone | 0.59 g | (0.0041 mole) |

The yield of monochloro compounds (hydroquinone, monoester, diester) based on the unchlorinated reactants (hydroquinone, monoester and diester) converted was 94.4%.

EXAMPLE 5

The following compounds were charged into a 500 ml glass reactor equipped with a stirrer, thermometer, heating device, vertical condenser and dropping funnel:

| | | |
|---|---|---|
| (i) Hydroquinone | 9.8 g | (0.0891 mole) |
| (ii) Hydroquinone diacetate | 51.8 g | (0.267 mole) |
| (iii) Anhydrous acetic acid | 246 ml | |
| (iv) p-Toluenesulfonic acid | 0.64 g | |

The above mixture was heated to boiling for 3 hours. The solution was then cooled to ambient temperature. 22.9 g, i.e., 0.170 mole, of sulfuryl chloride were then added dropwise over 30 minutes while the temperature was maintained at approximately 30° C.

0.1 g of para-toluenesulfonic acid was added, followed by 91.75 g (i.e., 0.9 mole) of acetic anhydride, to the above solution and the reaction mixture was heated overnight at 100° C.

The following products were identified and determined in the reaction mixture by HPLC:

| | | |
|---|---|---|
| (1) Hydroquinone diacetate | 38.8 g | (0.2 mole) |
| (2) Monochlorohydroquinone diacetate | 33.8 g | (0.148 mole) |

-continued

| | | |
|---|---|---|
| (3) 2,5-Dichlorohydroquinone diacetate | 1.28 g | (0.0049 mole) |

The yield of monochlorohydroquinone diacetate based on converted hydroquinone and hydroquinone diacetate was 94.8%.

EXAMPLE 6

The following compounds were charged into a 500 ml glass reactor equipped as in Example 5, but on which the dropping funnel had been replaced by a gas inlet dip-pipe:

| | | |
|---|---|---|
| (i) Hydroquinone | 8.92 g | (0.0811 mole) |
| (ii) Hydroquinone diacetate | 47.18 g | (0.2432 mole) |
| (iii) Anhydrous acetic acid | 224 ml | |
| (iv) p-Toluenesulfonic acid | 0.58 g | |

The above mixture was heated to boiling for 3 hours. The solution was then cooled to ambient temperature. Gaseous chlorine was then added for 44 minutes at a rate of 5 l/hr, i.e., 3.66 l (0.164 mole) while the temperature was maintained at about 20° C.

90 g (0.88 mole) of acetic anhydride and 0.1 g of para-toluenesulfonic acid were added and the solution was heated to boiling for 5 hours.

The following results were obtained after analysis of the reaction mass by HPLC:

| | | |
|---|---|---|
| (1) Hydroquinone diacetate | 34.53 g | (0.178 mole) |
| (2) Monochlorohydroquinone diacetate | 32.33 g | (0.1415 mole) |
| (3) 2,5-Dichlorohydroquinone diacetate | 0.75 g | (0.00285 mole) |

The yield of monochlorohydroquinone diacetate based on converted hydroquinone and hydroquinone diacetate was 96.7%.

EXAMPLE 7

The following compounds were charged into the 500 ml glass reactor employed in Example 6, fitted with a stirrer:

| | | |
|---|---|---|
| (i) Hydroquinone | 8.92 g | (0.0811 mole) |
| (ii) Hydroquinone diacetate | 47.18 g | (0.2432 mole) |
| (iii) Anhydrous acetic acid | 224 ml | |
| (iv) p-Toluenesulfonic acid | 0.52 g | |

The above mixture was heated to boiling for 3 hours. The solution was cooled slightly and then gaseous chlorine was added for 44 minutes at a rate of 5 l/hr, i.e., 3.66 l (0.164 mole) at a temperature of 80° C.

As soon as the chlorination was completed, 90 g (0.88 mole) of acetic anhydride and 0.1 g of p-toluenesulfonic acid were added and the solution was heated to boiling for 5 hours.

The following results were obtained after analysis of the reaction mixture by HPLC:

| | | |
|---|---|---|
| (1) Hydroquinone diacetate | | (0.194 mole) |
| (2) Monochlorohydroquinone diacetate | | (0.1155 mole) |
| (3) 2,5-Dichlorohydroquinone diacetate | | (0.0098 mole) |

The yield of monochlorohydroquinone diacetate based on converted hydroquinone and hydroquinone diacetate was 88.6%.

EXAMPLE 8

The procedure was as in Example 6, but a larger amount of chlorine, i.e., 3.815 l (0.170 mole) was added at 20° C.

The following results were obtained:

| | | |
|---|---|---|
| (1) Hydroquinone diacetate | 32.3 g | (0.1665 mole) |
| (2) Monochlorohydroquinone diacetate | 34.05 g | (0.149 mole) |
| (3) 2,5-Dichlorohydroquinone diacetate | 0.89 g | (0.0034 mole) |

The yield of monochlorohydroquinone diacetate based on converted hydroquinone diacetate and hydroquinone was 94.4%.

EXAMPLE 9

Into a 100 ml reactor equipped with a stirrer, thermometer, gas inlet dip-pipe and a cooling bath were charged:

| | | |
|---|---|---|
| (i) Hydroquinone | 1.56 g | (0.0142 mole) |
| (ii) Hydroquinone diacetate | 8.27 g | (0.0426 mole) |
| (iii) Triethylamine | 0.075 g | |
| (iv) Diisopropyl ether | 15 ml | |

The mixture was heated for 4 hours at 150° C. and then diisopropyl ether and triethylamine were stripped off by distillation under reduced pressure. The residue was dissolved in 45 ml of anhydrous acetic acid.

Gaseous chlorine was introduced into the solution, maintained at 20° C., at a rate of 5 l/hr for 6 minutes and 30 seconds, i.e., 0.54 l (0.024 mole).

When chlorine addition was completed, 10 ml of acetic anhydride and 0.015 g of para-toluenesulfonic acid were added.

The mixture was heated at 100° C. for 1 day.

The following were determined by HPLC in the final reaction mixture (weight 68.65 g):

| | | |
|---|---|---|
| (1) Hydroquinone diacetate | 6.5 g | (0.034 mole) |
| (2) Monochlorohydroquinone diacetate | 4.95 g | (0.022 mole) |
| (3) 2,5-Dichlorohydroquinone diacetate | 0.2 g | (0.0008 mole) |

The yield of monochlorohydroquinone diacetate based on converted hydroquinone and hydroquinone diacetate was 96.5%.

While this invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of a monohalohydroquinone monocarboxylate, comprising halogenating a hydroquinone monocarboxylate having the formula:

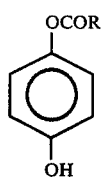

wherein R is a straight of branched chain alkyl radical containing from 1 to 4 carbon atoms, or an admixture of said hydroquinone monocarboxylate with a hydroquinone dicarboxylate and a minor amount of hydroquinone, said minor amount of hydroquinone being less than the amount of hydroquinone monocarboxylate and hydroquinone dicarboxylate with chlorine, bromine or sulfuryl halide halogenating agent, in a substantially anhydrous carboxylic acid reaction medium comprising an alkanoic acid having from 1 to 8 carbon atoms.

2. The process as defined by claim 1, which comprises halogenating admixture of a hydroquinone monocarboxylate, a hydroquinone dicarboxylic and a minor amount of hydroquinone, said admixture comprising reaction product from the partial acylation of hydroquinone.

3. The process as defined by claim 1, wherein said halogenating agent is chlorine.

4. The process of claim 1, further comprising separating monohalohydroquinone monocarboxylate from the other components of the medium.

5. The process as defined by claim 1, said substantially anhydrous carboxylic acid comprising an alkanoic acid having from 1 to 8 carbon atoms which is liquid under the conditions of halogenation.

6. The process as defined by claim 5, said substantially anhydrous carboxylic acid comprising acetic acid.

7. The process as defined by claim 1, the amount of halogenating agent ranging from 0.5 to 1.5 moles per mole of hydroquinone monocarboxylate.

8. The process as defined by claim 7, the temperature of halogenation ranging from 0° to 120° C.

9. The process of claim 7, further comprising separating monohalohydroquinone monocarboxylate from the other components of the medium.

10. The process as defined by claim 1, further comprising acylating resulting monohalohydroquinone monocarboxylate into monohalohydroquinone dicarboxylate.

11. The process as defined by claim 20, comprising carrying out said acylation in the presence of a catalytically effective amount of a strong acid having a pK of less than 1 in water at 25° C. in a carboxylic acid reaction medium which is liquid under the conditions of acylation.

12. The process as defined by claim 10, comprising directly acylating the halogenation reaction product.

13. The process as defined by claim 10, comprising acylating with an acylating agent which comprises acetic anhydride.

14. The process as defined by claim 10, comprising acylating with from 1 to 5 moles of acylating agent per mole of phenolic hydroxy group to be acylated.

15. The process as defined by claim 10, wherein R is methyl, said halogenating agent is chlorine and the monochlorohydroquinone monoacetate is acylated with acetic anydride or acetyl chloride.

16. A process for the preparation of a monohalohydroquinone monocarboxylate, comprising (i) first reacting a hydroquinone dicarboxylate with hydroquinone wherein the molar ratio of hydroquinone dicarboxylate to hydroquinone is at least 1.5, and thence (ii) halogenating the reaction admixture which results, comprising a hydroquinone monocarboxylate having the formula:

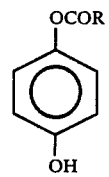

wherein R is a straight or branched chain alkyl radical containing from 1 to 4 carbon atoms, a hydroquinone dicarboxylate and a minor amount of hydroquinone, with chlorine, bromine or sulfuryl halide halogenating agent, in a substantially anhydrous carboxylic acid reaction medium comprising an alkanoic acid having from 1 to 8 carbon atoms.

17. The process as defined by claim 16, wherein said halogenating agent is chlorine.

18. The process as defined by claim 16, comprising carrying out said reaction (i) in the presence of a catalytically effective amount of a transesterification catalyst.

19. The process as defined by claim 16, comprising carrying out said reaction (i) in a carboxylic acid reaction medium which is liquid under the conditions of disproportionation.

20. The process as defined by claim 19, said alkanoic acid comprising acetic acid.

21. The process as defined by claim 19, comprising carrying out said reaction (i) in the presence of a catalytically effective amount of a strong acid having a pK of less than 1 in water at 25° C.

22. The process as defined by claim 21, said strong acid comprising sulfuric or an organosulfonic acid.

23. The process as defined by claim 21, comprising carrying out said reaction (i) in the presence of from 0.0001 to 0.2 equivalents of strong acid proton per mole of hydroquinone.

24. The process as defined by claim 16, comprising carrying out said reaction (i) in an aliphatic ether reaction medium in the presence of a catalytically effective amount of an organic nitrogenous base or Lewis acid catalyst.

25. The process as defined by claim 24, said catalyst comprising triethylamine.

26. The process as defined by claim 24, said aliphatic ether reaction medium comprising isopropyl ether.

27. The process as defined by claim 24, comprising carrying out said reaction (i) in the presence of from 0.0001 to 0.2 mole of said catalyst per mole of hydroquinone.

28. The process as defined by claim 16, further comprising acylating resulting monohalohydroquinone monocarboxylate into monohalohydroquinone dicarboxylate.

29. The process as defined by claim 28, comprising carrying out said acylation in the presence of a catalytically effective amount of a strong acid having a pK of less than 1 in water at 25° C., in a carboxylic acid reaction medium which is liquid under the conditions of acylation.

30. The process as defined by claim 28, comprising directly acylating the halogenation reaction product.

31. The process as defined by claim 28, comprising acylating with an acylating agent which comprises acetic anhydride.

32. The process as defined by claim 28, comprising acylating with from 1 to 5 moles of acylating agent per mole of phenolic hydroxy group to be acylated.

33. The process as defined by claim 28, further comprising separating the acylation reaction product into the individual components thereof and recycling separated hydroquinone dicarboxylate and carboxylic acid reaction medium to said disproportionation reaction (i).

34. The process as defined by claim 28, wherein R is methyl, said halogenating agent is chlorine and the monochlorohydroquinone monoacetate is acylated with acetic anhydride or acetyl chrloride.

* * * * *